(12) United States Patent
Berg et al.

(10) Patent No.: US 7,439,356 B2
(45) Date of Patent: Oct. 21, 2008

(54) SUBSTITUTED INDAN DERIVATIVES

(75) Inventors: Stefan Berg, Ekerö (SE); Lennart Florvall, Södertälje (SE); Svante Ross, Södertälje (SE); Seth-Olov Thorberg, Strängnäs (SE)

(73) Assignee: AstraZeneca AB, Sodertalje (SE)

( * ) Notice: Subject to any disclaimer, the term of this patent is extended or adjusted under 35 U.S.C. 154(b) by 121 days.

(21) Appl. No.: 11/543,250

(22) Filed: Oct. 3, 2006

(65) Prior Publication Data

US 2007/0149545 A1   Jun. 28, 2007

Related U.S. Application Data

(60) Continuation of application No. 10/807,918, filed on Mar. 24, 2004, now abandoned, which is a continuation of application No. 10/339,477, filed on Jan. 9, 2003, now abandoned, which is a division of application No. 09/171,575, filed as application No. PCT/SE98/01605 on Sep. 9, 1998, now Pat. No. 6,548,498.

(30) Foreign Application Priority Data

Sep. 18, 1997   (SE) .................................... 9703379

(51) Int. Cl.
C07D 265/30 (2006.01)
C07D 295/135 (2006.01)
C07D 211/26 (2006.01)
C07D 295/155 (2006.01)
A61K 31/495 (2006.01)
A61K 31/445 (2006.01)

(52) U.S. Cl. ...................... 544/166; 564/162; 564/163; 564/167; 564/168; 544/121; 544/160; 544/163; 544/402; 544/403; 514/235.5; 514/255.03

(58) Field of Classification Search ................. 544/160, 544/163, 166; 564/162, 163, 167, 168
See application file for complete search history.

(56) References Cited

U.S. PATENT DOCUMENTS 6,528,685 B2 * 3/2003 Cohen et al. ................ 564/215
6,878,707 B2 * 4/2005 Ksander ................... 514/237.8

FOREIGN PATENT DOCUMENTS

WO   WO 94/21619   9/1994
WO   WO 97/34883   9/1997

* cited by examiner

Primary Examiner—Peter G O'Sullivan
(74) Attorney, Agent, or Firm—White & Case LLP

(57) ABSTRACT

The present invention relates to intermediates of the formula

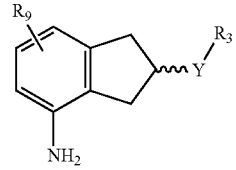

useful in the preparation of piperazinyl-substituted indan derivatives, wherein Y is $CONR_2$ wherein $R_2$ is H or $C_1$-$C_6$ alkyl;

$R_3$ is $C_1$-$C_6$ alkyl, $C_3$-$C_6$ cycloalkyl or $(CH_2)_n$-aryl, wherein aryl is phenyl or a heteroaromatic ring containing one or two heteroatoms selected from N, O and S and which may be mono- or di-substituted with $R_4$ and/or $R_5$, wherein $R_4$ and $R_5$ are as defined in the specification; and $R_9$ is H, $C_1$-$C_6$ alkyl, $C_3$-$C_6$ cycloalkyl, $OCF_3$, $OCHF_2$, $OCH_2F$, halogen, CN, $CF_3$, OH, $C_1$-$C_6$ alkoxy, $C_1$-$C_6$ alkoxy-$C_1$-$C_6$ alkyl, $NR_6R_7$, $SO_3CH_3$, $SO_3CF_3$, $SO_2NR_6R_7$, an unsubstituted or substituted heterocyclic or heteroaromatic ring containing one or two heteroatoms selected from N and O, wherein the substituent(s) is(are) $C_1$-$C_6$ alkyl; or $COR_8$; wherein $R_6$, $R_7$ and $R_8$ are as defined in the specification. The invention further relates to a process for the preparation of the intermediates.

3 Claims, 1 Drawing Sheet

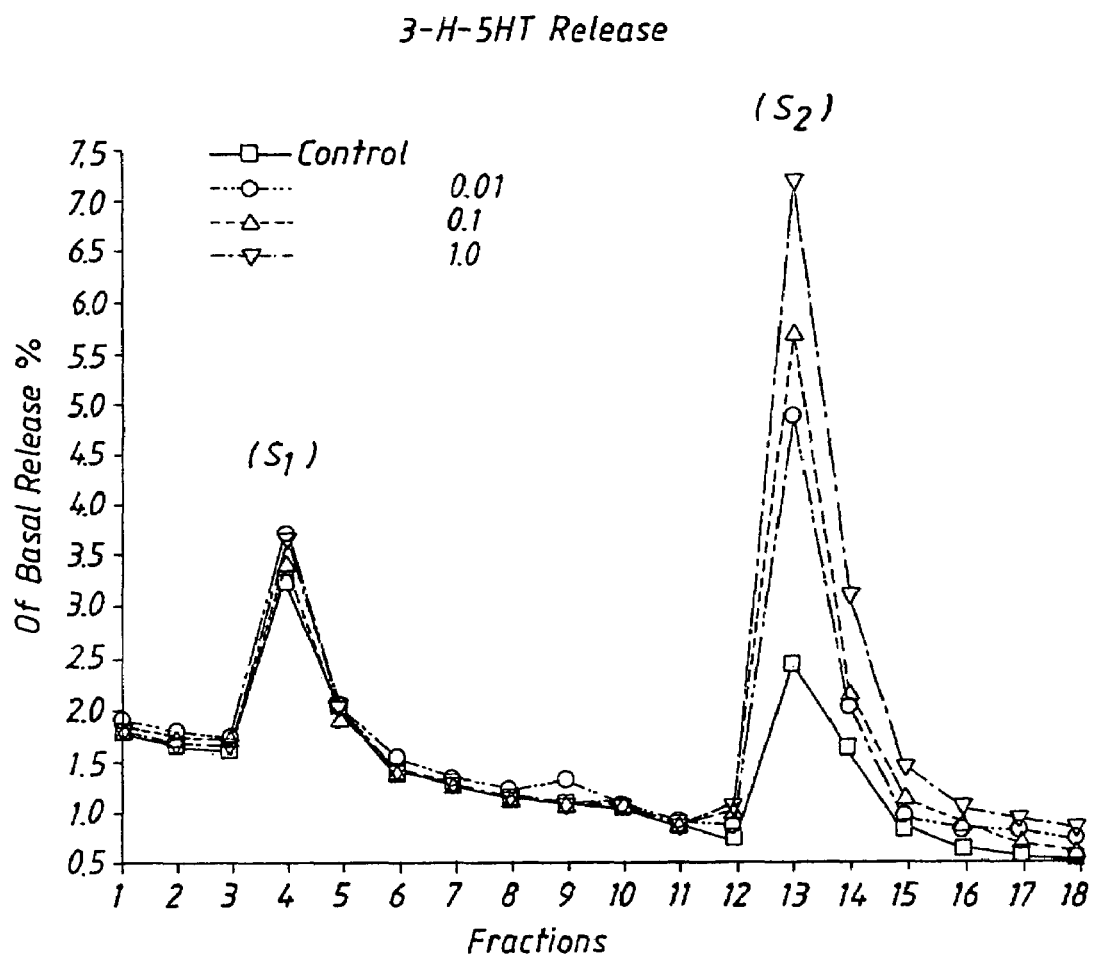

SUBSTITUTED INDAN DERIVATIVES

This application is a continuation of U.S. application Ser. No. 10/807,918, filed Mar. 24, 2004, now abandoned, which is a continuation of U.S. application Ser. No. 10/339,477, filed Jan. 9, 2003, now abandoned, which was a divisional of U.S. application Ser. No. 09/171,575, filed Oct. 21, 1998, U.S. Pat. No. 6,548,498, which was the National Stage of International Application No. PCT/SE98/01605, filed Sep. 9, 1998.

FIELD OF THE INVENTION

The present invention relates to new piperidyl- or piperazinyl-substituted indan derivatives as (R)-enantiomers, (S)-enantiomers or racemates in the form of free base or pharmaceutically acceptable salts or solvates thereof, a process for their preparation, pharmaceutical compositions containing said therapeutically active compounds and to the use of said active compounds in therapy.

An object of the invention is to provide compounds for therapeutic use, especially compounds having a selective effect at a subgroup of 5-hydroxytryptamine receptors, designated the h5-$HT_{1B}$-receptor (previously called the 5-$HT_{1D\beta}$-receptor) in mammals including man.

It is also an object of the invention to provide compounds with a therapeutic effect after oral administration.

BACKGROUND OF THE INVENTION

Various central nervous system disorders such as depression, anxiety, etc. appear to involve the disturbance of the neurotransmitters noradrenaline (NA) and 5-hydroxytryptamine (5-HT), the latter also known as serotonin. The drugs most frequently used in the treatment of depression are believed to act by improving the neurotransmission of either or both of these physiological agonists. It appears that the enhancement of 5-HT neurotransmission primarily affects the depressed mood and anxiety, whereas the enhancement of noradrenaline neurotransmission affects the retardation symptoms occurring in depressed patients. The invention concerns compounds which have an effect on 5-HT neurotransmission.

Serotonin, or 5-HT, activity is believed to be involved in many different types of psychiatric disorders. For instance it is believed that an increase in 5-HT activity is associated with anxiety, while a decrease in 5-HT release is associated with depression. Serotonin has in addition been implicated in such diverse conditions as eating disorders, gastrointestinal disorders, cardiovascular regulation disorders and sexual disturbances.

The 5-HT Receptors

The various effects of 5-HT may be related to the fact that serotoninergic neurons stimulate the secretion of several hormones, e.g. cortisol, prolactin, β-endorphin, vasopressin and others. The secretion of each of these other hormones appears to be regulated on a specific basis by several different 5-HT (serotonin) receptor subtypes. With the aid of molecular biology techniques, to date these receptors have been classified as 5-$HT_1$, 5-$HT_2$, 5-$HT_3$, 5-$HT_4$, 5-$HT_5$, 5-$HT_6$ and 5-$HT_7$ with the 5-$HT_1$ receptor further divided into the 5-$HT_{1A}$, 5-$HT_{1B}$, 5-$HT_{1D}$, 5-$HT_{1E}$ and 5-$HT_{1F}$ subtypes. Each receptor subtype is involved in a different serotonin function and has different properties.

Regulation of the 5-HT Transmission

The release of 5-HT is feedback-regulated by two different subtypes of 5-HT receptors. Inhibitory 5-$HT_{1A}$ autoreceptors are located on the cell bodies in the raphé nuclei which upon stimulation by 5-HT decrease the impulse propagation in the 5-HT neurons and thereby reducing the 5-HT released at the nerve terminals. Another subtype of inhibitory 5-HT receptors is located on the 5-HT nerve terminals, the h5-$HT_{1B}$ receptors (in rodents the r5-$HT_{1B}$ receptors) which regulate the synaptic concentration of 5-HT by controlling the amount of 5-HT that is released. An antagonist of these terminal autoreceptors thus increases the amount of 5-HT released by nerve impulses which has been shown in both in vitro and in vivo experiments.

The use of an antagonist of the terminal h5-$HT_{1B}$ autoreceptor will accordingly increase the synaptic 5-HT concentration and enhance the transmission in the 5-HT system. It would thus produce an antidepressant effect making it useful as a medication for depression.

Other localizations of h5-$HT_{1B}$ receptor subtype also exist. A large part of these postsynaptic receptors appear to be located on nerve terminals of other neuronal systems (so called heteroreceptors). Since the h5-$HT_{1B}$ receptor mediates inhibitory responses an antagonist of this receptor subtype might also increase the release of other neurotransmitters than 5-HT.

Compounds having h5-$HT_{1B}$ activity may according to well known and recognised pharmacological tests be divided into full agonists, partial agonists and antagonists.

BRIEF DESCRIPTION OF THE SINGLE DRAWING

FIG. 1 shows the dose-dependent effect of a tested h5-$HT_{1B}$ antagonist on the release of [$^3$H]-5-HT from guinea pig brain slices.

DISCLOSURE OF THE INVENTION

The object of the present invention is to provide compounds having a selective effect at the h5-$HT_{1B}$ receptor, preferably antagonistic properties, as well as having a good bioavailability. The effect on the other receptors chosen from, for example, the 5-$HT_{1A}$, 5-$HT_{2A}$, $D_1$, $D_{2A}$, $D_3$, $\alpha_1$ and $\alpha_2$ receptor has been investigated.

Accordingly, the present invention provides compounds of the formula I

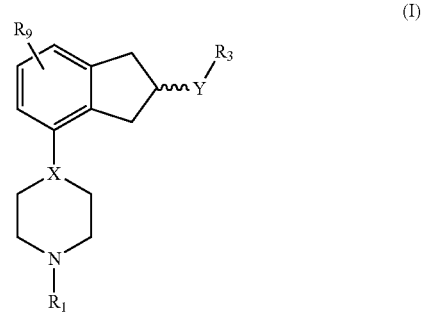

(I)

wherein
X is N or CH;
Y is $NR_2CH_2$, $CH_2NR_2$, $NR_2CO$, $CONR_2$ or $NR_2SO_2$
   wherein $R_2$ is H or $C_1$-$C_6$ alkyl;
$R_1$ is H, $C_1$-$C_6$ alkyl or $C_3$-$C_6$ cycloalkyl;

$R_3$ is $C_1$-$C_6$ alkyl, $C_3$-$C_6$ cycloalkyl or $(CH_2)_n$-aryl,
   wherein aryl is phenyl or a heteroaromatic ring containing one or two heteroatoms selected from N, O and S and which may be mono- or disubstituted with $R_4$ and/or $R_5$;
      wherein $R_4$ is H, $C_1$-$C_6$ alkyl, $C_3$-$C_6$ cycloalkyl, halogen, CN, $CF_3$, OH, $C_1$-$C_6$ alkoxy, $NR_6R_7$, $OCF_3$, $SO_3CH_3$, $SO_3CF_3$, $SO_2NR_6R_7$, phenyl, phenyl-$C_1$-$C_6$ alkyl, phenoxy, $C_1$-$C_6$ alkylphenyl, an optionally substituted heterocyclic ring containing one or two heteroatoms selected from N, O, S, SO and $SO_2$ wherein the substituent(s) is(are) selected from $C_1$-$C_6$ alkyl, $C_3$-$C_6$ cycloalkyl and phenyl-$C_1$-$C_6$ alkyl, an optionally substituted heteroaromatic ring containing one or two heteroatoms selected from N, O and S herein the substituent(s) is(are) selected from $C_1$-$C_6$ alkyl, $C_3$-$C_6$ cycloalkyl and phenyl-$C_1$-$C_6$ alkyl, or $COR_8$;
      wherein $R_6$ is H, $C_1$-$C_6$ alkyl or $C_3$-$C_6$ cycloalkyl;
      $R_7$ is H, $C_1$-$C_6$ alkyl or $C_3$-$C_6$ cycloalkyl; and
      $R_8$ is $C_1$-$C_6$ alkyl, $C_3$-$C_6$ cycloalkyl, $CF_3$, $NR_6R_7$, phenyl, a heteroaromatic ring containing one or two heteroatoms selected from N, O and S or a heterocyclic ring containing one or two heteroatoms selected from N, O, S, SO and $SO_2$;
      wherein $R_5$ is H, OH, $CF_3$, $OCF_3$, halogen, $C_1$-$C_6$ alkyl or $C_1$-$C_6$ alkoxy;
n is 0-4;
$R_9$ is H, $C_1$-$C_6$ alkyl, $C_3$-$C_6$ cycloalkyl, $OCF_3$, $OCHF_2$, $OCH_2F$, halogen, CN, $CF_3$, OH, $C_1$-$C_6$ alkoxy, $C_1$-$C_6$ alkoxy-$C_1$-$C_6$ alkyl, $NR_6R_7$, $SO_3CH_3$, $SO_3CF_3$, $SO_2NR_6R_7$, an unsubstituted or substituted heterocyclic or heteroaromatic ring containing one or two heteroatoms selected from N, O and S wherein the substituent(s) is(are) $C_1$-$C_6$ alkyl; or $COR_8$; wherein $R_6$, $R_7$ and $R_8$ are as defined above,
as (R)-enantiomers, (S)-enantiomers or a racemate in the form of a free base or a pharmaceutically acceptable salt or solvate thereof which possess a high selective effect at the h5-$HT_{1B}$ receptor and also show sufficient bioavailability after oral administration.

In the present context $C_1$-$C_6$ alkyl may be straight or branched. $C_1$-$C_6$ alkyl may be methyl, ethyl, n-propyl, i-propyl, n-butyl, i-butyl, s-butyl, t-butyl, n-pentyl, i-pentyl, t-pentyl, neo-pentyl, n-hexyl or i-hexyl.

In the present context $C_1$-$C_6$ alkoxy may be straight or branched. $C_1$-$C_6$ alkoxy may be methoxy, ethoxy, n-propoxy, i-propoxy, n-butoxy, i-butoxy, s-butoxy, t-butoxy, n-pentyloxy, i-pentyloxy, t-pentyloxy, neo-pentyloxy, n-hexyloxy or i-hexyloxy.

In the present context $C_3$-$C_6$ cycloalkyl may be cyclopropyl, cyclobutyl, cyclopentyl or cyclohexyl.

In the present context halogen may be fluoro, chloro, bromo or iodo.

In the present context the heteroaromatic ring containing one or two heteroatoms selected from N, O and S preferably is a 5- or 6-membered heteroaromatic ring and may be furyl, imidazolyl, isoxazolyl, isothiazolyl, oxazolyl, pyrazinyl, pyrazolyl, pyridazinyl, pyridyl, pyrimidyl, pyrrolyl, thiazolyl or thienyl. The heteroaromatic ring can be either substituted or unsubstituted.

In the present context the heterocyclic ring containing one or two heteroatoms selected from N, O, S, SO and $SO_2$ may optionally contain a carbonyl function and is preferably a 5-, 6- or 7-membered heterocyclic ring and may be imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl, thiomorpholinyl, preferably piperidino, 1-piperazinyl, morpholino, thiomorpholino and 4-piperidon-1-yl.

A preferred embodiment of the invention relates to compounds of formula I wherein Y is NHCO or CONH i.e. amides. Of these compounds, the compounds wherein $R_9$ is H, $C_1$-$C_6$ alkyl, $C_1$-$C_6$ alkoxy, $OCHF_2$ or $OCH_2F$ and $R_3$ is unsubstituted phenyl, or mono- or di-substituted phenyl, and especially ortho-, meta- or para-substituted phenyl, and particularly these wherein the substituent $R_4$ is phenyl, phenyl-$C_1$-$C_6$ alkyl, cyclohexyl, piperidino, 1-piperazinyl, morpholino, $CF_3$, 4-piperidon-1-yl, n-butoxy or $COR_8$ wherein $R_8$ is phenyl, cyclohexyl, 4-piperidon-1-yl, 1-piperazinyl, morpholino, $CF_3$, piperidino or $NR_6R_7$, are preferred.

Examples of Combinations of Substituents are:

X is N, Y is $CONR_2$, $R_1$ is H, $CH_3$, $C_2H_5$ or $C_3H_7$, $R_2$ is H, $R_3$ is $CH_2$-phenyl, $R_9$ is $CH_3$, $C_2H_5$ or $C_3H_7$;

X is N, Y is $CONR_2$, $R_1$ is H, $CH_3$, $C_2H_5$ or $C_3H_7$, $R_2$ is H, $R_3$ is $(CH_2)_2$-phenyl, $R_4$ is piperidino, $R_5$ and $R_9$ are H;

X is CH, Y is $CONR_2$, $R_1$ is H, $CH_3$, $C_2H_5$ or $C_3H_7$, $R_2$ is H, $R_3$ is phenyl, $R_4$ is phenyl, phenylmethyl or phenylethyl, $R_5$ is H, $R_9$ is $OCH_3$;

X is N, Y is $NR_2CO$, $R_1$ is H, $CH_3$, $C_2H_5$ or $C_3H_7$, $R_2$ is H, $R_3$ is $(CH_2)_2$-phenyl, $R_4$ is phenyl, phenylmethyl or phenylethyl, $R_5$ and $R_9$ are H;

X is CH, Y is $CONR_2$, $R_1$ is H, $CH_3$, $C_2H_5$ or $C_3H_7$, $R_2$ is H, $R_3$ is $CH_2$-phenyl, $R_4$ is piperidino, $R_5$ is H, $R_9$ is $CH_3$, $C_2H_5$ or $C_3H_7$;

X is N, Y is $NR_2CO$, $R_1$ is H, $CH_3$, $C_2H_5$ or $C_3H_7$, $R_2$ is H, $R_3$ is $(CH_2)_2$-phenyl, $R_4$ is piperidino, $R_5$ is H, $R_9$ is $OCH_3$;

X is N, Y is $NR_2CO$, $R_1$ is H, $CH_3$, $C_2H_5$ or $C_3H_7$, $R_2$ is H, $R_3$ is phenyl, $R_4$ is piperidino, $R_5$ and $R_9$ are H;

X is CH, Y is $NR_2CO$, $R_1$ is H, $CH_3$, $C_2H_5$ or $C_3H_7$, $R_2$ is H, $R_3$ is $CH_2$-phenyl, $R_9$ is $OCH_3$;

X is N, Y is $NR_2CO$, $R_1$ is H, $CH_3$, $C_2H_5$ or $C_3H_7$, $R_2$ is H, $R_3$ is $(CH_2)_2$-phenyl, $R_4$ is morpholino, $R_5$ is H, $R_9$ is $CH_3$, $C_2H_5$ or $C_3H_7$;

X is CH, Y is $CONR_2$, $R_1$ is H, $CH_3$, $C_2H_5$ or $C_3H_7$, $R_2$ is H, $R_3$ is $CH_2$-phenyl, $R_4$ is phenyl, phenylmethyl or phenylethyl, $R_5$ and $R_9$ are H;

X is CH, Y is $CONR_2$, $R_1$ is H, $CH_3$, $C_2H_5$ or $C_3H_7$, $R_2$ is H, $R_3$ is phenyl, $R_4$ is morpholino, $R_5$ is H, $R_9$ is $OCH_3$;

X is CH, Y is $NR_2CO$, $R_1$ is H, $CH_3$, $C_2H_5$ or $C_3H_7$, $R_2$ is H, $R_3$ is phenyl, $R_4$ is piperidino, $R_5$ and $R_9$ are H;

X is CH, Y is $CONR_2$, $R_1$ is H, $CH_3$, $C_2H_5$ or $C_3H_7$, $R_2$ is H, $R_3$ is $(CH_2)_2$-phenyl, $R_4$ is piperidino, $R_5$ is H, $R_9$ is $CH_3$, $C_2H_5$ or $C_3H_7$;

X is N, Y is $NR_2CO$, $R_1$ is H, $CH_3$, $C_2H_5$ or $C_3H_7$, $R_2$ is H, $R_3$ is $(CH_2)_2$-phenyl, $R_5$ and $R_9$ are H;

X is CH, Y is $NR_2CO$, $R_1$ is H, $CH_3$, $C_2H_5$ or $C_3H_7$, $R_2$ is H, $R_3$ is $CH_2$-phenyl, $R_4$ is phenyl, phenylmethyl or phenylethyl, $R_5$ is H, $R_9$ is $OCH_3$;

X is CH, Y is $CONR_2$, $R_1$ is H, $CH_3$, $C_2H_5$ or $C_3H_7$, $R_2$ is H, $R_3$ is $CH_2$-phenyl, $R_5$ and $R_9$ are H;

X is N, Y is $CONR_2$, $R_1$ is H, $CH_3$, $C_2H_5$ or $C_3H_7$, $R_2$ is H, $R_3$ is phenyl, $R_9$ is $CH_3$, $C_2H_5$ or $C_3H_7$;

X is N, Y is $CONR_2$, $R_1$ is H, $CH_3$, $C_2H_5$ or $C_3H_7$, $R_2$ is H, $R_3$ is $(CH_2)_2$-phenyl, $R_4$ is piperidino, $R_5$ is H, $R_9$ is $OCH_3$;

X is N, Y is $NR_2CO$, $R_1$ is H, $CH_3$, $C_2H_5$ or $C_3H_7$, $R_2$ is H, $R_3$ is $CH_2$-phenyl, $R_4$ is phenyl, phenylmethyl or phenylethyl, $R_5$ and $R_9$ are H;

X is CH, Y is $CONR_2$, $R_1$ is H, $CH_3$, $C_2H_5$ or $C_3H_7$, $R_2$ is H, $R_3$ is phenyl, $R_4$ is piperidino, $R_5$ is H, $R_9$ is $OCH_3$;

X is CH, Y is $NR_2CO$, $R_1$ is H, $CH_3$, $C_2H_5$ or $C_3H_7$, $R_2$ is H, $R_3$ is phenyl, $R_4$ is morpholino, $R_5$ and $R_9$ are H;

X is N, Y is CONR$_2$, R$_1$ is H, CH$_3$, C$_2$H$_5$ or C$_3$H$_7$, R$_2$ is H, R$_3$ is phenyl, R$_4$ is COR$_8$, R$_8$ is cyclohexyl, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is phenyl, R$_4$ is morpholino, R$_5$ and R$_9$ are H;

X is N, Y is NR$_2$CO, R$_1$ is H, CH$_3$, C$_2$H$_5$ or C$_3$H$_7$, R$_2$ is H, R$_3$ is CH$_2$-phenyl, R$_4$ is morpholino, R$_5$ is H, R$_9$ is OCH$_3$;

X is N, Y is NR$_2$CO, R$_1$ is H, CH$_3$, C$_2$H$_5$ or C$_3$H$_7$, R$_2$ is H, R$_3$ is CH$_2$-phenyl, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is piperidino, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is phenyl, R$_4$ is piperidino, R$_5$ is H, R$_9$ is OCH$_3$;

X is CH, Y is CONR$_2$, R$_1$ is H, CH$_3$, C$_2$H$_5$ or C$_3$H$_7$, R$_2$ is H, R$_3$ is phenyl, R$_4$ is piperidino, R$_5$ and R$_9$ are H;

X is CH, Y is NR$_2$CO, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is CH$_2$-phenyl, R$_4$ is morpholino, R$_5$ and R$_9$ are H;

X is N, Y is CONR$_2$, R$_1$ is H, CH$_3$, C$_2$H$_5$ or C$_3$H$_7$, R$_2$ is H, R$_3$ is CH$_2$-phenyl, R$_4$ is morpholino, R$_5$ is H, R$_9$ is OCH$_3$;

X is N, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ is H, R$_9$ is OCH$_3$;

X is N, Y is NR$_2$CO, R$_1$ is H, CH$_3$, C$_2$H$_5$ or C$_3$H$_7$, R$_2$ is H, R$_3$ is CH$_2$-phenyl, R$_4$ is morpholino, R$_5$ and R$_9$ are H;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_9$ is OCH$_3$;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is piperidino, R$_5$ and R$_9$ are H;

X is N, Y is CONR$_2$, R$_1$ is H, CH$_3$, C$_2$H$_5$ or C$_3$H$_7$, R$_2$ is H, R$_3$ is phenyl, R$_4$ is morpholino, R$_5$ is H, R$_9$ is OCH$_3$;

X is CH, Y is CONR$_2$, R$_1$ is H, CH$_3$, C$_2$H$_5$ or C$_3$H$_7$, R$_2$ is H, R$_3$ is phenyl, R$_9$ is H;

X is N, Y is CONR$_2$, R$_1$ is H, CH$_3$, C$_2$H$_5$ or C$_3$H$_7$, R$_2$ is H, R$_3$ is CH$_2$-phenyl, R$_4$ is piperidino, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is phenyl, R$_4$ is morpholino, R$_5$ and R$_9$ are H;

X is N, Y is CONR$_2$, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is phenyl, R$_4$ is piperidino, R$_5$ and R$_9$ are H;

X is CH, Y is CONR$_2$, R$_1$ is H, CH$_3$, C$_2$H$_5$ or C$_3$H$_7$, R$_2$ is H, R$_3$ is phenyl, R$_9$ is OCH$_3$;

X is CH, Y is NR$_2$CO, R$_1$ is H, CH$_3$, C$_2$H$_5$ or C$_3$H$_7$, R$_2$ is H, R$_3$ is CH$_2$-phenyl;

X is N, Y is NR$_2$CO, R$_1$ is H, CH$_3$, C$_2$H$_5$ or C$_3$H$_7$, R$_2$ is H, R$_3$ is phenyl, R$_4$ is morpholino, R$_5$ is H, R$_9$ is OCH$_3$;

X is CH, Y is NR$_2$CO, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ and R$_9$ are H;

X is N, Y is NR$_2$CO, R$_1$ is H, CH$_3$, C$_2$H$_5$ or C$_3$H$_7$, R$_2$ is H, R$_3$ is phenyl, R$_4$ is piperidino, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_9$ is H;

X is N, Y is CONR$_2$, R$_1$ is H, CH$_3$, C$_2$H$_5$ or C$_3$H$_7$, R$_2$ is H, R$_3$ is CH$_2$-phenyl, R$_4$ is morpholino, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is morpholino, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is CH$_2$-phenyl, R$_4$ is piperidino, R$_5$ and R$_9$ are H;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is piperidino, R$_5$ is H, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is piperidino, R$_5$ and R$_9$ are H;

X is N, Y is CONR$_2$, R$_1$ is H, CH$_3$, C$_2$H$_5$ or C$_3$H$_7$, R$_2$ is H, R$_3$ is CH$_2$-phenyl, R$_9$ is OCH$_3$;

X is N, Y is CONR$_2$, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ and R$_9$ are H;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ is H, R$_9$ is OCH$_3$;

X is N, Y is NR$_2$CO, R$_1$ is H, CH$_3$, C$_2$H$_5$ or C$_3$H$_7$, R$_2$ is H, R$_3$ is phenyl, R$_4$ is morpholino, R$_5$ and R$_9$ are H;

X is N, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ is H, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is CH$_2$-phenyl, R$_4$ is piperidino, R$_5$ and R$_9$ are H;

X is N, Y is NR$_2$CO, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is CH$_2$-phenyl;

X is N, Y is NR$_2$CO, R$_1$ is H, CH$_3$, C$_2$H$_5$ or C$_3$H$_7$, R$_2$ is H, R$_3$ is (CH$_2$)$_2$-phenyl, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is CH$_2$-phenyl, R$_4$ is piperidino, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is morpholino, R$_5$ and R$_9$ are H;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is piperidino, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is phenyl, R$_4$ is COR$_8$, R$_8$ is morpholino, R$_9$ is H;

X is N, Y is CONR$_2$, R$_1$ is H, CH$_3$, C$_2$H$_5$ or C$_3$H$_7$, R$_2$ is H, R$_3$ is phenyl, R$_4$ is COR$_8$, R$_8$ is morpholino, R$_9$ is OCH$_3$;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is morpholino, R$_5$ is H, R$_9$ is OCH$_3$;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is phenyl, phenylmethyl or phenylethyl, R$_5$ and R$_9$ are H;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is morpholino, R$_5$ is H, R$_9$ is OCH$_3$;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is morpholino, R$_5$ and R$_9$ are H;

X is CH, Y is CONR$_2$, R$_1$ is H, CH$_3$, C$_2$H$_5$ or C$_3$H$_7$, R$_2$ is H, R$_3$ is CH$_2$-phenyl, R$_4$ is phenyl, phenylmethyl or phenylethyl, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ and R$_9$ are H;

X is N, Y is NR$_2$CO, R$_1$ is H, CH$_3$, C$_2$H$_5$ or C$_3$H$_7$, R$_2$ is H, R$_3$ is phenyl, R$_4$ is COR$_8$, R$_8$ is morpholino, R$_9$ is OCH$_3$;

X is N, Y is NR$_2$CO, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ and R$_9$ are H;

X is CH, Y is NR$_2$CO, R$_1$ is H, CH$_3$, C$_2$H$_5$ or C$_3$H$_7$, R$_2$ is H, R$_3$ is phenyl, R$_9$ is OCH$_3$;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is piperidino, R$_5$ and R$_9$ are H;

X is N, Y is NR$_2$CO, R$_1$ is H, CH$_3$, C$_2$H$_5$ or C$_3$H$_7$, R$_2$ is H, R$_3$ is phenyl, R$_9$ is OCH$_3$;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is COR$_8$, R$_8$ is NR$_6$R$_7$, R$_6$R$_7$CH$_3$, C$_2$H$_5$ or C$_3$H$_7$ and R$_9$ is H;

X is CH, Y is CONR$_2$, R$_1$ is H, CH$_3$, C$_2$H$_5$ or C$_3$H$_7$, R$_2$ is H, R$_3$ is phenyl, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ and R$_9$ are H;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ is H, R$_9$ is OCH$_3$;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is morpholino, R$_5$ and R$_9$ are H;

X is N, Y is CONR$_2$, R$_1$ is H, CH$_3$, C$_2$H$_5$ or C$_3$H$_7$, R$_2$ is H, R$_3$ is CH$_2$-phenyl, R$_4$ is phenyl, phenylmethyl or phenylethyl, R$_5$ is H, R$_9$ is OCH$_3$;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_9$ is H;

X is CH, Y is NR$_2$CO, R$_1$ is H, CH$_3$, C$_2$H$_5$ or C$_3$H$_7$, R$_2$ is H, R$_3$ is phenyl, R$_4$ is piperidino, R$_5$ is H, R$_9$ is OCH$_3$;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ and R$_9$ are H;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_9$ is OCH$_3$;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is morpholino, R$_5$ and R$_9$ are H;

X is N, Y is CONR$_2$, R$_1$ is H, CH$_3$, C$_2$H$_5$ or C$_3$H$_7$, R$_2$ is H, R$_3$ is phenyl, R$_4$ is COR$_8$, R$_8$ is cyclohexyl, R$_9$ is OCH$_3$;

X is N, Y is NR$_2$CO, R$_1$ is H, CH$_3$, C$_2$H$_5$ or C$_3$H$_7$, R$_2$ is H, R$_3$ is phenyl, R$_4$ is COR$_8$, R$_8$ is morpholino, R$_9$ is H;

X is N, Y is CONR$_2$, R$_1$ is H, CH$_3$, C$_2$H$_5$ or C$_3$H$_7$, R$_2$ is H, R$_3$ is phenyl, R$_9$ is OCH$_3$;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_9$ is H;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is COR$_8$, R$_8$ is NR$_6$R$_7$, R$_6$R$_7$CH$_3$, C$_2$H$_5$ or C$_3$H$_7$, R$_9$ is OCH$_3$;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ and R$_9$ are H;

X is N, Y is NR$_2$CO, R$_1$ is H, CH$_3$, C$_2$H$_5$ or C$_3$H$_7$, R$_2$ is H, R$_3$ is CH$_2$-phenyl, R$_9$ is OCH$_3$.

X is CH, Y is CONR$_2$, R$_1$ is H, CH$_3$, C$_2$H$_5$ or C$_3$H$_7$, R$_2$ is H, R$_3$ is CH$_2$-phenyl, R$_4$ is morpholino, R$_5$ and R$_9$ are H;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is phenyl, R$_9$ is H;

X is CH, Y is CONR$_2$, R$_1$ is H, CH$_3$, C$_2$H$_5$ or C$_3$H$_7$, R$_2$ is H, R$_3$ is CH$_2$-phenyl, R$_4$ is morpholino, R$_5$ is H, R$_9$ is OCH$_3$;

X is N, Y is NR$_2$CO, R$_1$ is H, CH$_3$, C$_2$H$_5$ or C$_3$H$_7$, R$_2$ is H, R$_3$ is phenyl, R$_9$ is H;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_9$ is OCH$_3$;

X is N, Y is NR$_2$CO, R$_1$ is H, CH$_3$, C$_2$H$_5$ or C$_3$H$_7$, R$_2$ is H, R$_3$ is phenyl, R$_4$ is piperidino, R$_5$ is H, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is CH$_2$-phenyl, R$_4$ is piperidino, R$_5$ and R$_9$ are H;

X is CH, Y is NR$_2$CO, R$_1$ is H, CH$_3$, C$_2$H$_5$ or C$_3$H$_7$, R$_2$ is H, R$_3$ is phenyl, R$_4$ is piperidino, R$_5$ is H, R$_9$ is CH$_3$, C$_2$H$_5$ or C$_3$H$_7$;

X is N, Y is CONR$_2$, R$_1$ is H, CH$_3$, C$_2$H$_5$ or C$_3$H$_7$, R$_2$ is H, R$_3$ is CH$_2$-phenyl, R$_4$ is phenyl, phenylmethyl or phenylethyl, R$_5$ and R$_9$ are H;

X is CH, Y is CONR$_2$, R$_1$ is H, CH$_3$, C$_2$H$_5$ or C$_3$H$_7$, R$_2$ is H, R$_3$ is CH$_2$-phenyl, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is piperidino, R$_5$ and R$_9$ are H;

X is N, Y is NR$_2$CO, R$_1$ is H, CH$_3$, C$_2$H$_5$ or C$_3$H$_7$, R$_2$ is H, R$_3$ is (CH$_2$)$_2$-phenyl, R$_9$ is OCH$_3$;

X is N, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is piperidino, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is morpholino, R$_5$ is H, R$_9$ is OCH$_3$;

X is N, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is morpholino, R$_5$ and R$_9$ are H;

X is CH, Y is CONR$_2$, R$_1$ is H, CH$_3$, C$_2$H$_5$ or C$_3$H$_7$, R$_2$ is H, R$_3$ is CH$_2$-phenyl, R$_4$ is phenyl, phenylmethyl or phenylethyl, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is COR$_8$, R$_8$ is NR$_6$R$_7$, R$_6$R$_7$CH$_3$, C$_2$H$_5$ or C$_3$H$_7$, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is piperidino, R$_5$ and R$_9$ are H;

X is N, Y is NR$_2$CO, R$_1$ is H, CH$_3$, C$_2$H$_5$ or C$_3$H$_7$, R$_2$ is H, R$_3$ is CH$_2$-phenyl, R$_4$ is phenyl, phenylmethyl or phenylethyl, R$_5$ is H, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is CH$_2$-phenyl, R$_4$ is morpholino, R$_5$ is H, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is CH$_2$-phenyl, R$_4$ is piperidino, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is phenyl, R$_4$ is COR$_8$, R$_8$ is cyclohexyl, R$_9$ is H;

X is CH, Y is CONR$_2$, R$_1$ is H, CH$_3$, C$_2$H$_5$ or C$_3$H$_7$, R$_2$ is H, R$_3$ is phenyl, R$_4$ is morpholino, R$_5$ is H, R$_9$ is CH$_3$, C$_2$H$_5$ or C$_3$H$_7$;

X is N, Y is CONR$_2$, R$_1$ is H, CH$_3$, C$_2$H$_5$ or C$_3$H$_7$, R$_2$ is H, R$_3$ is phenyl, R$_4$ is morpholino, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is phenyl, R$_4$ is morpholino, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is piperidino, R$_5$ is H, R$_9$ is CH$_3$, C$_2$H$_5$ or C$_3$H$_7$;

X is N, Y is CONR$_2$, R$_1$ is H, CH$_3$, C$_2$H$_5$ or C$_3$H$_7$, R$_2$ is H, R$_3$ is phenyl, R$_9$ is H;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ is H, R$_9$ is OCH$_3$;

X is CH, Y is CONR$_2$, R$_1$ is H, CH$_3$, C$_2$H$_5$ or C$_3$H$_7$, R$_2$ is H, R$_3$ is CH$_2$-phenyl, R$_9$ is OCH$_3$;

X is N, Y is NR$_2$CO, R$_1$ is H, CH$_3$, C$_2$H$_5$ or C$_3$H$_7$, R$_2$ is H, R$_3$ is CH$_2$-phenyl, R$_4$ is piperidino, R$_5$ is H, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is phenyl, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is CH$_2$-phenyl, R$_9$ is H;

X is CH, Y is NR$_2$CO, R$_1$ is H, CH$_3$, C$_2$H$_5$ or C$_3$H$_7$, R$_2$ is H, R$_3$ is CH$_2$-phenyl, R$_9$ is CH$_3$, C$_2$H$_5$ or C$_3$H$_7$;

X is N, Y is CONR$_2$, R$_1$ is H, CH$_3$, C$_2$H$_5$ or C$_3$H$_7$, R$_2$ is H, R$_3$ is phenyl, R$_4$ is piperidino, R$_5$ is H, R$_9$ is CH$_3$, C$_2$H$_5$ or C$_3$H$_7$ X is CH, Y is NR$_2$CO, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is piperidino, R$_5$ is H, R$_9$ is CH$_3$, C$_2$H$_5$ or C$_3$H$_7$;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_9$ is CH$_3$, C$_2$H$_5$ or C$_3$H$_7$;

X is N, Y is $NR_2CO$, $R_1$ is H, $CH_3$, $C_2H_5$ or $C_3H_7$, $R_2$ is H, $R_3$ is phenyl, $R_4$ is phenyl, phenylmethyl or phenylethyl, $R_5$ is H, $R_9$ is $CH_3$, $C_2H_5$ or $C_3H_7$;

X is N, Y is $CONR_2$, $R_1$ is H, $CH_3$, $C_2H_5$ or $C_3H_7$, $R_2$ is H, $R_3$ is phenyl, $R_4$ is phenyl, phenylmethyl or phenylethyl, $R_5$ is H, $R_9$ is $CH_3$, $C_2H_5$ or $C_3H_7$;

X is CH, Y is $CONR_2$, $R_1$ is H, $CH_3$, $C_2H_5$ or $C_3H_7$, $R_2$ is H, $R_3$ is phenyl, $R_4$ is piperidino, $R_5$ is H, $R_9$ is $CH_3$, $C_2H_5$ or $C_3H_7$;

X is CH, Y is $CONR_2$, $R_1$ is H, $CH_3$, $C_2H_5$ or $C_3H_7$, $R_2$ is H, $R_3$ is $CH_2$-phenyl, $R_4$ is morpholino, $R_5$ is H, $R_9$ is $CH_3$, $C_2H_5$ or $C_3H_7$;

X is N, Y is $CONR_2$, $R_1$ is H, $CH_3$, $C_2H_5$ or $C_3H_7$, $R_2$ is H, $R_3$ is $(CH_2)_2$-phenyl, $R_4$ is morpholino, $R_5$ is H, $R_9$ is $CH_3$, $C_2H_5$ or $C_3H_7$;

X is N, Y is $NR_2CO$, $R_1$ is H, $CH_3$, $C_2H_5$ or $C_3H_7$, $R_2$ is H, $R_3$ is $CH_2$-phenyl, $R_4$ is phenyl, phenylmethyl or phenylethyl, $R_5$ is H, $R_9$ is $OCH_3$;

X is N, Y is $CONR_2$, $R_1$ is H, $CH_3$, $C_2H_5$ or $C_3H_7$, $R_2$ is H, $R_3$ is phenyl, $R_4$ is $COR_8$, $R_8$ is morpholino, $R_9$ is $CH_3$, $C_2H_5$ or $C_3H_7$;

X is CH, Y is $NR_2CO$, $R_1$ is H, $CH_3$, $C_2H_5$ or $C_3H_7$, $R_2$ is H, $R_3$ is $(CH_2)_2$-phenyl, $R_4$ is morpholino, $R_5$ is H, $R_9$ is $CH_3$, $C_2H_5$ or $C_3H_7$;

X is N, Y is $NR_2CO$, $R_1$ is H, $CH_3$, $C_2H_5$ or $C_3H_7$, $R_2$ is H, $R_3$ is phenyl, $R_4$ is morpholino, $R_5$ is H, $R_9$ is $CH_3$, $C_2H_5$ or $C_3H_7$;

X is N, Y is $CONR_2$, $R_1$ is H, $CH_3$, $C_2H_5$ or $C_3H_7$, $R_2$ is H, $R_3$ is $(CH_2)_2$-phenyl, $R_4$ is phenyl, phenylmethyl or phenylethyl, $R_5$ is H, $R_9$ is $CH_3$, $C_2H_5$ or $C_3H_7$;

X is CH, Y is $NR_2CO$, $R_1$ is H, $CH_3$, $C_2H_5$ or $C_3H_7$, $R_2$ is H, $R_3$ is phenyl, $R_4$ is morpholino, $R_5$ is H, $R_9$ is $OCH_3$;

X is CH, Y is $CONR_2$, $R_1$ is H, $CH_3$, $C_2H_5$ or $C_3H_7$, $R_2$ is H, $R_3$ is phenyl, $R_4$ is phenyl, phenylmethyl or phenylethyl, $R_5$ is H, $R_9$ is $CH_3$, $C_2H_5$ or $C_3H_7$;

X is N, Y is $NR_2CO$, $R_1$ is H, $CH_3$, $C_2H_5$ or $C_3H_7$, $R_2$ is H, $R_3$ is phenyl, $R_4$ is $COR_8$, $R_8$ is morpholino, $R_9$ is $CH_3$, $C_2H_5$ or $C_3H_7$;

X is CH, Y is $CONR_2$, $R_1$ is H, $CH_3$, $C_2H_5$ or $C_3H_7$, $R_2$ is H, $R_3$ is $(CH_2)_2$-phenyl, $R_4$ is morpholino, $R_5$ is H, $R_9$ is $CH_3$, $C_2H_5$ or $C_3H_7$;

X is CH, Y is $CONR_2$, $R_1$ is H, $CH_3$, $C_2H_5$ or $C_3H_7$, $R_2$ is H, $R_3$ is $(CH_2)_2$-phenyl, $R_4$ is phenyl, phenylmethyl or phenylethyl, $R_5$ is H, $R_9$ is $CH_3$, $C_2H_5$ or $C_3H_7$;

X is CH, Y is $NR_2CO$, $R_1$ is H, $CH_3$, $C_2H_5$ or $C_3H_7$, $R_2$ is H, $R_3$ is phenyl, $R_9$ is $CH_3$, $C_2H_5$ or $C_3H_7$;

X is N, Y is $CONR_2$, $R_1$ is H, $CH_3$, $C_2H_5$ or $C_3H_7$, $R_2$ is H, $R_3$ is $CH_2$-phenyl, $R_4$ is phenyl, phenylmethyl or phenylethyl, $R_5$ is H, $R_9$ is $CH_3$, $C_2H_5$ or $C_3H_7$;

X is CH, Y is $NR_2CO$, $R_1$ is H, $CH_3$, $C_2H_5$ or $C_3H_7$, $R_2$ is H, $R_3$ is $CH_2$-phenyl, $R_4$ is morpholino, $R_5$ is H, $R_9$ is $CH_3$, $C_2H_5$ or $C_3H_7$;

X is CH, Y is $CONR_2$, $R_1$ is H, $CH_3$, $C_2H_5$ or $C_3H_7$, $R_2$ is H, $R_3$ is $(CH_2)_2$-phenyl, $R_4$ is piperidino, $R_5$ is H, $R_9$ is $OCH_3$;

X is N, Y is $NR_2CO$, $R_1$ is H, $CH_3$, $C_2H_5$ or $C_3H_7$, $R_2$ is H, $R_3$ is $(CH_2)_2$-phenyl, $R_4$ is morpholino, $R_5$ is H, $R_9$ is $OCH_3$;

X is CH, Y is $NR_2CO$, $R_1$ is H, $CH_3$, $C_2H_5$ or $C_3H_7$, $R_2$ is H, $R_3$ is $(CH_2)_2$-phenyl, $R_4$ is phenyl, phenylmethyl or phenylethyl, $R_5$ is H, $R_9$ is $CH_3$, $C_2H_5$ or $C_3H_7$;

X is N, Y is $CONR_2$, $R_1$ is H, $CH_3$, $C_2H_5$ or $C_3H_7$, $R_2$ is H, $R_3$ is $CH_2$-phenyl, $R_4$ is piperidino, $R_5$ is H, $R_9$ is $CH_3$, $C_2H_5$ or $C_3H_7$;

X is CH, Y is $CONR_2$, $R_1$ is H, $CH_3$, $C_2H_5$ or $C_3H_7$, $R_2$ is H, $R_3$ is $(CH_2)_2$-phenyl, $R_9$ is $CH_3$, $C_2H_5$ or $C_3H_7$;

X is CH, Y is $NR_2CO$, $R_1$ is H, $CH_3$, $C_2H_5$ or $C_3H_7$, $R_2$ is H, $R_3$ is $CH_2$-phenyl, $R_4$ is phenyl, phenylmethyl or phenylethyl, $R_5$ is H, $R_9$ is $CH_3$, $C_2H_5$ or $C_3H_7$.

A preferred compound is 4-(4-methylpiperazin-1-yl)-N-(4-morpholinophenyl)-indan-2-carboxamide.

The compounds of the present invention are in the form of the racemate or the (R)- or (S)-enantiomer in the form of a free base or a pharmaceutically acceptable salt or solvate thereof Compounds in the form of the (R)-enantiomer are believed to be preferred ones.

Both organic and inorganic acids can be employed to form non-toxic pharmaceutically acceptable acid addition salts of the compounds of this invention. Illustrative acids are sulfuric, nitric, phosphoric, oxalic, hydrochloric, formic, hydrobromic, citric, acetic, lactic, tartaric, dibenzoyltartaric, diacetyltartaric, palmoic, ethanedisulfonic, sulfamic, succinic, propionic, glycolic, malic, gluconic, pyruvic, phenylacetic, 4-aminobenzoic, anthranilic, salicylic, 4-aminosalicylic, 4-hydroxybenzoic, 3,4-dihydroxybenzoic, 3,5-dihydroxybenzoic, 3-hydroxy-2-naphthoic, nicotinic, methanesulfonic, ethanesulfonic, hydroxyethanesulfonic, benzenesulfonic, p-toluenesulfonic, sulfanilic, naphthalenesulfonic, ascorbic, cyclohexylsulfamic, fumaric, maleic and benzoic acids. These salts are readily prepared by methods known in the art.

The preferred solvates of the compounds of this invention are the hydrates.

Pharmaceutical Formulations

In a second aspect the present invention provides a pharmaceutical formulation comprising as active ingredient a therapeutically effective amount of the compound of formula I as an enantiomer or a racemate in the form of a free base or a pharmaceutically acceptable salt or solvate thereof, optionally in association with diluents, excipients or inert carriers.

According to the present invention the compound of the invention will normally be administered orally, rectally or by injection, in the form of pharmaceutical formulations comprising the active ingredient either as a free base or a pharmaceutically acceptable non-toxic acid addition salt, e.g. the hydrochloride, hydrobromide, lactate, acetate, phosphate, sulfate, sulfamate, citrate, tartrate, oxalate and the like, in a pharmaceutically acceptable dosage form. The dosage form may be a solid, semisolid or liquid preparation. Usually the active substance will constitute between 0.1 and 99% by weight of the preparation, more specifically between 0.5 and 20% by weight for preparations intended for injection and between 0.2 and 50% by weight for preparations suitable for oral administration.

To produce pharmaceutical formulations containing the compound of the invention in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or poly-vinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a polymer known to the person skilled in the art, dissolved in a readily volatile organic solvent or mixture of organic solvents. Dyestuffs may be added to these coatings in order to readily distinguish between tablets containing different active substances or different amounts of the active compound.

For the preparation of soft gelatine capsules, the active substance may be admixed with e.g. a vegetable oil or polyethylene glycol. Hard gelatine capsules may contain granules of the active substance using either the above mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in a mixture with a neutral fatty base, or gelatine rectal capsules comprising the active substance in admixture with vegetable oil or paraffin oil. Liquid preparations for oral application may be in the form of syrups or suspensions, for example solutions containing from about 0.1% to about 20% by weight of the active substance herein described, the balance being sugar and mixture of ethanol, water, glycerol and propylene glycol. Optionally such liquid preparations may contain colouring agents, flavouring agents, saccharine and carboxymethyl-cellulose as a thickening agent or other excipients known to the person skilled in the art.

Solutions for parenteral applications by injection can be prepared in an aqueous solution of a water-soluble pharmaceutically acceptable salt of the active substance, preferably in a concentration of from about 0.1% to about 10% by weight. These solutions may also contain stabilizing agents and/or buffering agents and may conveniently be provided in various dosage unit ampoules.

Suitable daily doses of the compound of the invention in therapeutical treatment of humans are about 0.01-100 mg/kg bodyweight at peroral administration and 0.001-100 mg/kg bodyweight at parenteral administration.

The compounds of the invention may be used in a combination with a 5-HT reuptake inhibitor, such as fluoxetine, paroxetine, citalopram, clomipramine, sertraline, alaproclate or fluvoxamin, preferably paroxetine or citalopram. Another possible combination is to use the compound of the invention together with a monoamine oxidase inhibitor, such as moclobemide, tranylcypramine, brofaromide or phenelzine, preferably moclobemide or phenelzine. Still another possible combination is the compound of the invention together with a 5-HT$_{1A}$ antagonist, such as the compounds disclosed in WO 96/33710, preferably (R)-5-carbamoyl-3-(N,N-dicyclobutylamino)-8-fluoro-3,4-dihydro-2H-1-benzopyran.

Medical and Pharmaceutical Use

In a further aspect the present invention provides the use of the compounds of formula I in therapy as a h5-HT$_{1B}$ antagonist, partial agonist or full agonist, preferably as an antagonist and the use in the treatment of 5-hydroxytryptamine mediated disorders. Examples of such disorders are disorders in the CNS such as mood disorders (depression, major depressive episodes, dysthymia, seasonal affective disorder, depressive phases of bipolar disorder), anxiety disorders (obsessive compulsive disorder, panic disorder with/without agoraphobia, social phobia, specific phobia, generalized anxiety disorder, posttraumatic stress disorder), personality disorders (disorders of impulse control, trichotellomania), obesity, anorexia, bulimia, premenstrual syndrome, sexual disturbances, alcoholism, tobacco abuse, autism, attention deficit, hyperactivity disorder, migraine, memory disorders (age associated memory impairment, presenile and senile dementia), pathological aggression, schizophrenia, endocrine disorders (e g hyperprolactinaemia), stroke, dyskinesia, Parkinson's disease, thermoregulation, pain and hypertension. Other examples of hydroxytryptamine mediated disorders are urinary incontinence, vasospasm and growth control of tumors (e g lung carcinoma).

Methods of Preparation

The present invention also relates to processes for preparing the compound of formula I. Throughout the following description of such processes it is understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis" T. W. Greene, Wiley-Interscience, New York, 1991.

Methods of Preparation of Intermediates

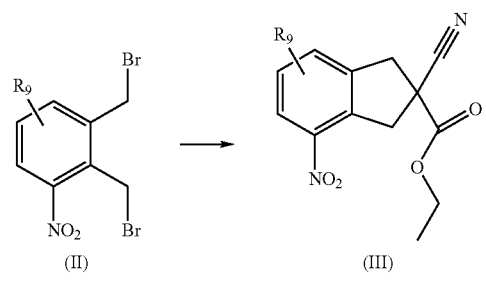

(i) Cyclization of the compound of formula II, where R$_9$ is hydrogen, to a compound of formula III, where R$_9$ is hydrogen, may be carried out in a suitable solvent such as N,N-dimethylformamide or dimethylsulfoxide in the presence of ethyl cyanoacetate and a suitable base such as K$_2$CO$_3$ or KOH. The reaction may occur between +20° C. and 100° C.

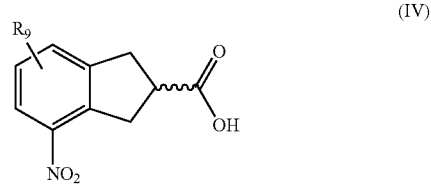

(ii) Conversion of a compound of formula III, where R$_9$ is hydrogen, to a compound of formula IV, where R$_9$ is hydrogen, may be carried by hydrolysis followed by decarboxylation under acidic conditions using acids such as HCl, HBr or H$_2$SO$_4$ in a suitable solvent such as acetic acid, water or mixtures thereof The reaction may occur between +20° C. and reflux. Hydrolysis under basic conditions may be carried out by using bases such as NaOH or KOH in a suitable solvent such as water, ethanol, methanol or mixtures thereof followed by decarboxylation under acidic conditions using acids such as HCl, HBr or H$_2$SO$_4$ in a suitable solvent such as acetic acid, water or mixtures thereof. The reaction may occur between +20° C. and reflux.

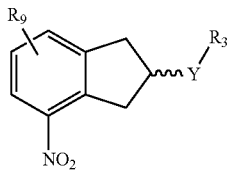

(V)

(iii) Conversion of a compound of formula IV, where $R_9$ is hydrogen, to a compound of formula V, where Y is $CONR_2$ and $R_9$ is hydrogen, may be carried out by activation of the acid function of a compound of formula IV as an acid halide such as an acid chloride with a suitable base such as a trialkylamine, e.g. triethylamine, or by using an activating reagent such as N,N'-carbonyldiimidazole, N,N-dicyclohexylcarbodiimide or diphenylphosphinic chloride with a suitable base such as N-methylmorpholine in a suitable solvent, e.g. methylene chloride, chloroform, toluene, N,N-dimethylformamide, dioxane or tetrahydrofuran, followed by the addition of an appropriate amine or aniline $HNR_2R_3$, where $R_2$ and $R_3$ are as in formula I above and the reaction may occur between 0° C. and +120° C.

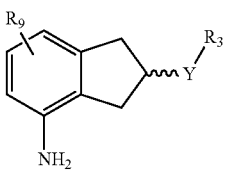

(VI)

(iv) Conversion of a compound of formula V to a compound of formula VI, where Y is $CONR_2$, $R_2$ and $R_3$ are as in formula I above, may be carried out by hydrogenation using a catalyst containing palladium, platinum, nickel or rhodium in a suitable solvent such as ethanol, methanol or acetic acid at a reaction temperature between +20° C. and +120° C.; or by reduction with a suitable reductive reagent such as sodium dithionite in a suitable solvent such as N,N-dimethylformamide at a reaction temperature between +20° C. and +120° C.

Methods of Preparation of End Products

Another object of the invention is a process for the preparation of the compound of general formula I by reacting, in the case where Y is $CONR_2$; $R_1$, $R_2$, $R_3$ and $R_9$ are as defined in general formula I above, a compound of formula A

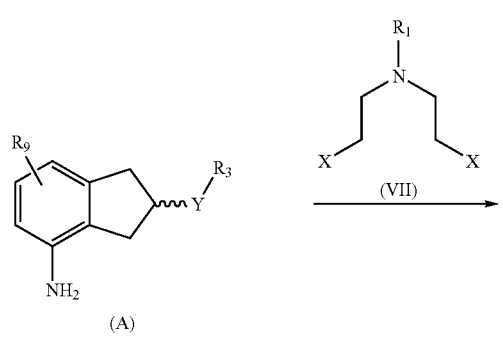

(A) (VII)

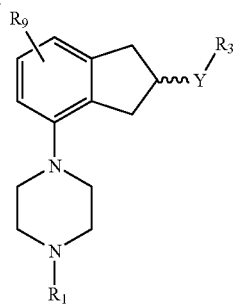

(I)

with a compound of formula VII wherein X is a leaving group.

Thus, the reaction according to the process A may be carried out with a compound of formula VII wherein X is a leaving group, e.g. a halogen such as chlorine or bromine or an alkane- or arenesulfonyloxy group such as p-toluenesulfonyloxy group. The process may be carried out in a suitable solvent such as ethanol, butanol, N,N-dimethylformamide, acetonitrile or a mixture of water and acetonitrile with or without a suitable base, e.g. $K_2CO_3$, $NaHCO_3$ or KOH, and the reaction may occur between +20° C. and +150° C.

Intermediates

Another object of the invention is a compound having the formula

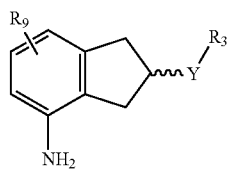

wherein

Y is $CONR_2$ wherein $R_2$ is H or $C_1$-$C_6$ alkyl, $R_3$ is $C_1$-$C_6$ alkyl, $C_3$-$C_6$ cycloalkyl or $(CH_2)_n$-aryl, wherein aryl is phenyl or a heteroaromatic ring containing one or two heteroatoms selected from N, O and S and which may be mono- or di-substituted with $R_4$ and/or $R_5$; wherein $R_4$, $R_5$ and n are as defined above;

$R_9$ is H, $C_1$-$C_6$ alkyl, $C_3$-$C_6$ cycloalkyl, $OCF_3$, $OCHF_2$, $OCH_2F$, halogen, CN, $CF_3$, OH, $C_1$-$C_6$ alkoxy, $C_1$-$C_6$ alkoxy-$C_1$-$C_6$ alkyl, $NR_6R_7$, $SO_3CH_3$, $SO_3CF_3$, $SO_2NR_6R_7$, an unsubstituted or substituted heterocyclic or heteroaromatic ring containing one or two heteroatoms selected from N and O, wherein the substituent(s) is(are) $C_1$-$C_6$ alkyl; or $COR_8$; wherein $R_6$, $R_7$ and $R_8$ are as defined above.

The invention is illustrated but not restricted to the following working examples.

WORKING EXAMPLES

Example 1

2-Cyano-2-ethoxycarbonyl-4-nitroindan

A mixture of 2,3-di(bromomethyl)nitrobenzene (34 g, 0.11 mol; described in: EP 0529 636 A1), potassium carbonate (35 g, 0.25 mol) and ethyl cyanoacetate (12 mL, 0.11 mmol) in N,N-dimethylformamide (50 mL) was stirred at room temperature for 48 h. The solvent was evaporated in vacuo and the residue was stirred with ethyl acetate. The mixture was filtered and the filtrate was washed with water and dried over sodium sulfate. The solvent was evaporated in vacuo to yield 29 g of the title compound as an oil (94% GC purity): EIMS (70 eV) m/z (relative intensity) 260 (4, M$^+$).

Example 2

4-Nitroindan-2-carboxylic acid

A mixture of 2-cyano-2-ethoxycarbonyl-4-nitroindan (21 g, 81 mmol), acetic acid (290 mL), hydrochloric acid (37%, 130 mL) and water (140 mL) was stirred under reflux temperature over night. The acid was evaporated in vacuo and the residue was made alkaline with a 2 M sodium hydroxide solution. The mixture was stirred at room temperature, insoluble matter was filtered and the filtrate was acidified with hydrochloric acid. The obtained precipitate was filtered and washed with water to afford 18 grain of the crude acid: mp ~140° C.; EIMS (70 eV) m/z (relative intensity) 207 (40, M$^+$).

Example 3

4-Amino-N-(4-morpholinophenyl)indan-2-carboxamide

A mixture of 4-nitroindan-2-carboxylic acid (2.2 g, 11 mmol), thionyl chloride (8.0 mL) and a catalytical amount of N,N-dimethylformamide in methylene chloride (20 mL) was stirred at reflux for 45 minutes. The solvent was evaporated in vacuo and the residue was dissolved in dry tetrahydrofuran and added, while stirring, to a mixture of 4-anilino-morpholine (1.7 g, 9 mmol) and potassium carbonate (3.0 g, 22 mmol) in acetonitrile (20 mL). The mixture was stirred for 1 h at 50° C. After the addition of water (250 mL), the obtained precipitate was filtered, washed with water and dried to afford 2.9 g (78% yield) of crude 4-nitro-N-(4-morpholinophenyl) indan-2-carboxamide: EIMS (70 eV) m/z (relative intensity) 367 (100, M$^+$).

To a solution of the crude nitro compound (3.5 g) in N,N-dimethylformamide (25 mL) and water (3 mL) was added, in portions, sodium dithionite (7.0 g, 40 mmol). The mixture was stirred at 90° C. for 3 hours. The solvent was evaporated in vacuo and water (200 mL) was added. The mixture was made alkaline with 2 M sodium hydroxide and extracted with chloroform. The phases were separated and the organic phase was dried (Na$_2$SO$_4$), filtered and evaporated in vacuo to give 1.1 g of the crude product (GC purity 89%): EIMS (70 eV) m/z (relative intensity) 337 (100, M$^+$).

Example 4

4-(4-Methylpiperazin-1-yl)-N-(4-morpholinophenyl) indan-2-carboxamide

A mixture of 4-amino-N-(4-morpholinophenyl)indan-2-carboxamide (1.1 g, 3 mmol), N-methyl-bis-(2-chloroethyl) amine hydrochloride (2.0 g, 10 mmol) and sodium hydrogen carbonate (8.0 g, 95 mmol) in 1-butanol (100 mL) was stirred overnight at 120° C. The mixture was filtered and the solvent was evaporated in vacuo. The crude residue (oil) was purified on a silica gel column using methylene chloride as the eluent to afford 100 mg of the title compound: mp 248-249° C.; EIMS (70 eV) m/z (relative intensity) 420 (47, M$^+$).

Pharmacology

Electrical Field Stimulation of [$^3$H]-5-HT Release from Occipital Cortex of Guinea Pigs

[$^3$H]-5-HT is released by electrical field stimulation from slices of occipital cortex of guinea pigs which have been pre-incubated with [$^3$H]-5-HT. This release is similar to that caused by nerve stimulation, i.e. exocytotic release from serotonergic nerve terminals, depending on the presence of Ca$^{2+}$ in the incubation medium. The 5-HT release is regulated at the level of the nerve terminals by autoreceptors, in the guinea pigs (like in humans) belonging to the h5-HT$_{1B}$ receptor subtype. Thus, agonists of h5-HT$_{1B}$ receptors reduce the amount of [$^3$H]-5-HT released by electrical field stimulation whereas the release is increased by antagonists of this receptor type. Testing compounds with this method is accordingly a convenient screening technique for determining the potency and functional effect of new h5-HT$_{1B}$ receptor agonists and antagonists.

Methods and Materials

Buffer composition (mM) NaHCO$_3$ (25), NaH$_2$PO$_4$.H$_2$O (1.2), NaCl (117), KCl(6), MgSO$_4$×7H$_2$O(1.2), CaCl$_2$(1.3), EDTA Na$_2$(0.03). The buffer is gassed for at least 30 min before use. The pH of the buffer is about 7.2 at room temperature but it rises to about 7.4 at 37° C.

Preparation of Occipital Cortical Slices

Guinea pigs (200-250 g) were decapitated and the whole brains were removed. The occipital cortices were dissected and cut into slices 0.4×4 mm with a McIlwain chopper machine. The white part of the tissue should be removed carefully with a tweezer before slicing. The slices were incubated in 5 ml buffer in the presence of 5 mM pargyline chloride. After incubation with 0.1 mM [$^3$H]-5-HT for another 30 min the slices were transferred to a test tube and washed three times with same volume buffer. The slices were transferred to the superfusion chambers with a plastic pipette and were washed for 40 min with the buffer in the presence of the uptake inhibitor citalopram 2.5 µM with a flow rate of 0.5 ml/min.

Electrical Stimulation of 5-HT Release

The superfused buffer was collected in 2 mL/fraction. The slices were stimulated by electricity with a train of pulses of frequency 3 Hz, duration 2 ms and current 30 mA for 3 min at the 4th and 13th fractions. The tested drugs were added from the 8th fraction to the end of experiment.

Results

A first electrical (or K$^+$) stimulation results in a standard amount of [$^3$H]-5-HT released (S$_1$). Between the first and the second stimulation the h5-HT$_{1B}$ antagonist is added to the media which results in a dose-dependent increase of the release(S$_2$) after the second stimulation. See FIG. 1.

The S$_2$/S$_1$ ratio, which is the per cent of released [$^3$H]-5-HT at the second stimulation (S$_2$) divided by that of the first stimulation (S$_1$), was used to estimate drug effects on transmitter release.

The invention claimed is:
1. A compound of the formula

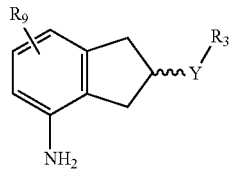

wherein
Y is $CONR_2$ wherein $R_2$ is H or $C_1$-$C_6$ alkyl;
$R_3$ is $C_1$-$C_6$ alkyl, $C_3$-$C_6$ cycloalkyl or $(CH_2)_n$-aryl,
wherein aryl is phenyl or a heteroaromatic ring containing one or two heteroatoms selected from N, O and S and which may be mono- or di-substituted with $R_4$ and/or $R_5$;
wherein $R_4$ is H, $C_1$-$C_6$ alkyl, $C_3$-$C_6$ cycloalkyl, halogen, CN, $CF_3$, OH, $C_1$-$C_6$ alkoxy, $NR_6R_7$, $OCF_3$, $SO_3CH_3$, $SO_3CF_3$, $SO_2NR_6R_7$, phenyl, phenyl-$C_1$-$C_6$ alkyl, phenoxy, $C_1$-$C_6$ alkylphenyl, an optionally substituted heterocyclic ring containing one or two heteroatoms selected from N, O, S, SO and $SO_2$ wherein the substituent(s) is(are) selected from $C_1$-$C_6$ alkyl, $C_3$-$C_6$ cycloalkyl and phenyl-$C_1$-$C_6$ alkyl, an optionally substituted heteroaromatic ring containing one or two heteroatoms selected from N, O and S wherein the substituent(s) is (are) selected from $C_1$-$C_6$ alkyl, $C_3$-$C_6$ cycloalkyl and phenyl-$C_1$-$C_6$ alkyl, or $COR_8$;
wherein $R_6$ is H, $C_1$-$C_6$ alkyl or $C_3$-$C_6$ cycloalkyl;
$R_7$ is H, $C_1$-$C_6$ alkyl or $C_3$-$C_6$ cycloalkyl; and
$R_8$ is $C_1$-$C_6$ alkyl, $C_3$-$C_6$ cycloalkyl, $CF_3$, $NR_6R_7$, phenyl, a heteroaromatic ring containing one or two heteroatoms selected from N, O and S or a heterocyclic ring containing one or two heteroatoms selected from N, O, S, SO and $SO_2$ wherein $R_6$ and $R_7$ are as defined above;
wherein $R_5$ is H, OH, $CF_3$, $OCF_3$, halogen, $C_1$-$C_6$ alkyl or $C_1$-$C_6$ alkoxy; n is 0-4;
and
$R_9$ is H, $C_1$-$C_6$ alkyl, $C_3$-$C_6$ cycloalkyl, $OCF_3$, $OCHF_2$, $OCH_2F$, halogen, CN, $CF_3$, OH, $C_1$-$C_6$ alkoxy, $C_1$-$C_6$ alkoxy-$C_1$-$C_6$ alkyl, $NR_6R_7$, $SO_3CH_3$, $SO_3CF_3$, $SO_2NR_6R_7$, an unsubstituted or substituted heterocyclic or heteroaromatic ring containing one or two heteroatoms selected from N and O, wherein the substituent(s) is(are) $C_1$-$C_6$ alkyl; or $COR_8$; wherein $R_6$, $R_7$ and $R_8$ are as defined above.

2. A process for the preparation of the compound of claim 1, which comprises the steps of

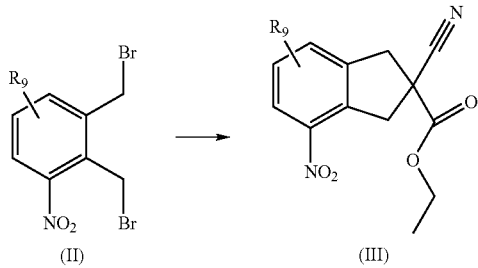

(i) Cyclization of the compound of formula II to a compound of formula III in a suitable solvent in the presence of ethyl cyanoacetate and a suitable base at a temperature between +20° C. and 100° C.;

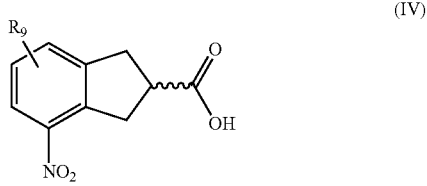

(ii) Conversion of a compound of formula III to a compound of formula IV, either by a) hydrolysis under acidic condition followed by decarboxylation under acidic conditions using a suitable acid in a suitable solvent at a temperature between +20° C. and reflux or b) hydrolysis under basic conditions using a suitable base in a suitable solvent followed by decarboxylation under acidic conditions using a suitable acid in a suitable solvent at a temperature between +20° C. and reflux;

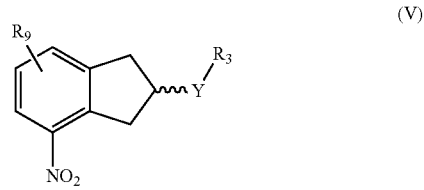

(iii) Conversion of a compound of formula IV to a compound of formula V, either by a) activation of the acid function of a compound of formula IV as an acid halide with a suitable base or by b) using an activating reagent with a suitable base in a suitable solvent, followed by the addition of an appropriate amine or aniline $HNR_2R_3$, where $R_2$ and $R_3$ are as defined in claim 1 at a temperature between 0° C. and +120° C.; and

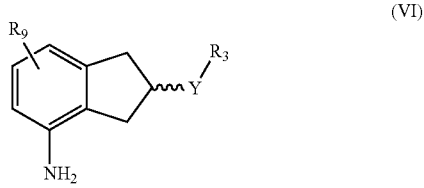

(iv) Conversion of a compound of formula V to a compound of formula VI, either by a) hydrogenation using a catalyst containing palladium, platinum, nickel or rhodium in a suitable solvent at a reaction temperature between +20° C. and +120° C. or b) by reduction with a suitable reductive reagent in a suitable solvent at a reaction temperature between +20° C. and +120° C.

3. The process according to claim 2, wherein
in step (i), the solvent is selected from N,N-dimethylformamide or dimethylsulfoxide and the base is selected from $K_2CO_3$ or KOH;
in step (ii), the hydrolysis and decarboxylation steps under acidic conditions are both carried out in an acid selected from HCl, HBr or $H_2SO_4$ and a solvent selected from acetic acid, water or a mixture thereof or the hydrolysis/decarboxylation process is carried out by hydrolysis under basic conditions in a base selected from NaOH or KOH and a solvent selected from water, ethanol, methanol or a mixture thereof followed by decarboxylation under acidic conditions using an acid selected from HCl, HBr or $H_2SO_4$ and a solvent selected from acetic acid, water or a mixture thereof;

in step (iii), the activation is carried out either a) with an acid halide with a trialkylamine as the base or b) with an activating agent selected from N,N-carbonyldiimidazole, N,N-dicyclohexylcarbodiimide or diphenylphosphinic chloride with N-methylmorpholine as the base in a solvent selected from methylene chloride, chloroform, toluene, N,N-dimethylformamide, dioxane or tetrahydrofuran; and in step (iv), the conversion is carried out either by a) catalytic hydrogenation in a solvent selected from ethanol, methanol or acetic acid or by b) reduction with sodium dithionite in N,N-dimethylformamide as solvent.

* * * * *